United States Patent [19]

Hatinguais et al.

[11] 4,436,749

[45] Mar. 13, 1984

[54] COMPOUNDS OF THE BENZOXEPINE SERIES AND SULPHUR- AND NITROGEN-CONTAINING ANALOGUES; THEIR PROCESSES FOR THE PREPARATION OF THESE PRODUCTS AND THE USE THEREOF IN THE PHARMACEUTICAL FIELD

[75] Inventors: Philippe Hatinguais; Jean-Francois Patoiseau; Gilbert Marcelon, all of Castres, France

[73] Assignee: Pierre Fabre S.A., Paris, France

[21] Appl. No.: 376,645

[22] Filed: May 10, 1982

[30] Foreign Application Priority Data

May 11, 1981 [FR] France ............................. 81 09327
May 4, 1982 [FR] France ............................. 82 07693

[51] Int. Cl.³ ................ C07D 313/08; C07D 337/08; C07D 223/16; A61K 31/335; A61K 31/55; A61K 31/38
[52] U.S. Cl. .................................... 424/278; 549/355; 549/9; 260/239 BB
[58] Field of Search ............ 549/355, 9; 260/239 BB; 424/278

[56] References Cited

U.S. PATENT DOCUMENTS 3,374,245 3/1968 Carney et al. ..................... 549/355

Primary Examiner—Norma S. Milestone
Attorney, Agent, or Firm—Fleit, Jacobson, Cohn & Price

[57] ABSTRACT

A compound corresponding to formula (I):

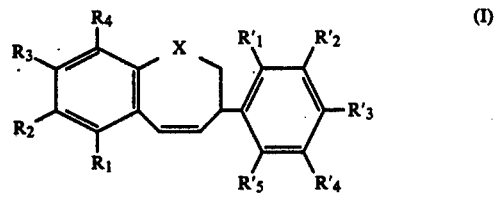

wherein
X represents oxygen, sulphur or $>N-R'$,
R' representing hydrogen or an alkyl radical,
$R_1$ to $R_4$, and
$R'_1$ to $R'_5$ independently represent the following:
  a hydrogen or halogen atom,
  an alkyl, aryl, alkoxy, aryloxy or acyloxy radical,
  a hydroxy radical,
  an amino, mono-alkylamino or di-alkylamino radical,
  a hydroxyalkyl, aminoalkoxy, mono- or di-alkylaminoalkoxy radical, in the form of the d or l isomer, or in the form of a racemic mixture, is useful as a medicament.

5 Claims, No Drawings

COMPOUNDS OF THE BENZOXEPINE SERIES AND SULPHUR- AND NITROGEN-CONTAINING ANALOGUES; THEIR PROCESSES FOR THE PREPARATION OF THESE PRODUCTS AND THE USE THEREOF IN THE PHARMACEUTICAL FIELD

This invention relates to new compounds of the benzoxepine series and sulphur- and nitrogen-containing analogues.

This invention also relates to processes for the preparation of these products and the use thereof in the pharmaceutical field.

Although benzoxepines form a chemical class which includes numerous compounds, none of the known compounds has been described as having pharmacological properties in the cardiovascular field.

We have discovered that 3-phenyl-2,3-dihydro-1-benzoxepines and the analogues thereof in the benzazepine and benzothiepine series of new chemical compounds have most valuable properties in the cardiovascular field.

The invention relates to compounds corresponding to the formula:

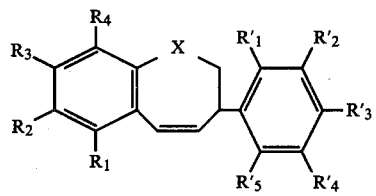
(I)

wherein

X represents oxygen, sulphur or >N—R′,

R′ representing hydrogen or an alkyl radical;

$R_1$ to $R_4$, and $R'_1$ to $R'_5$ independently represent the following:

a hydrogen or halogen atom, an alkyl, aryl, alkoxy, aryloxy or acyloxy radical, a hydroxy radical, an amino, mono-alkylamino or di-alkylamino radical, a hydroxyalkyl, aminoalkoxy, mono- or di-alkylaminoalkoxy radical.

Among these compounds, those in which the radicals $R_1$ to $R_4$ and $R'_1$ to $R'_5$ represent a hydrogen atom, a hydroxy radical or a methoxy radical are of particular interest.

Moreover, the compounds corresponding to the following formula should also be mentioned:

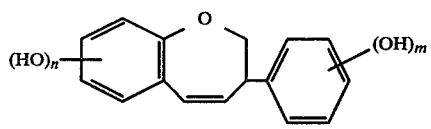

wherein n is an integer from 0 to 4, and m is an integer from 0 to 5; and above all the compounds corresponding to the following formula:

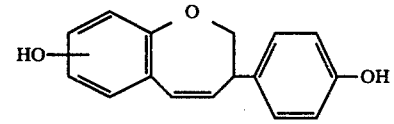

in the form of d or l isomers or in the form of a racemic mixture.

It should be noted that the compounds according to the present invention contain an asymmetric carbon atom in the 3-position and may thus either be in the form of a racemic mixture or two isomeric forms, either in a levorotatory form or in a dextrorotatory form.

Of course, the present invention relates both to racemic mixtures as well as to pure d or l isomers, or mixtures enriched with one of the two isomers.

Moreover, it is clear that, depending on the type of compound which is used, one of the isomers or the racemic mixture will be able to present more advantageous properties for a particular use.

The term "alkyl radical" as used herein is understood to designate more particularly lower $C_1$ to $C_5$ alkyl radicals, and preferably $C_1$ to $C_3$ radicals.

The alkoxy radicals which are particularly preferred are those which correspond to the alkyl radicals which have previously been mentioned.

The aryl radicals are more particularly aromatic carbocyclic or heterocyclic radicals containing from 5 to 12 atoms in the rings, the phenyl radical being preferred. The aryloxy radicals which are preferred are those corresponding to the aryl radicals previously mentioned.

The acyloxy radicals are preferably radicals corresponding to $C_2$ to $C_7$ alkanoic acids.

The significance of the other radicals which have been mentioned is easily deduced from the definitions provided above.

The present invention also relates to processes for the preparation of the compounds according to this invention.

The compounds of the present invention may notably be prepared by one of the following processes.

In a first type of process, a compound corresponding to formula II is dehydrated:

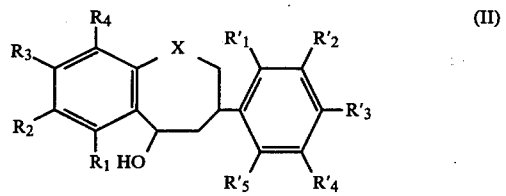
(II)

preferably in the presence of p-toluene sulphonic acid.

The compound corresponding to formula II may be prepared as will be explained in the following from the corresponding ketone.

In a second synthesis method, the compounds according to the present invention are prepared by the decarboxylation of a compound corresponding to formula III:

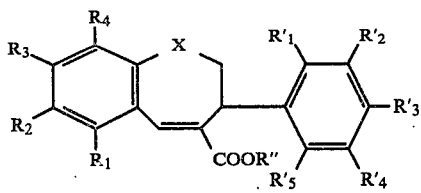

(III)

wherein R" is an alkyl radical, dècarboxylation preferably being carried out in the presence of copper chromite and quinoline at a temperature of from 150° to 300° C., preferably at a temperature of about 200° C.

When the compound according to the present invention contains free hydroxy radicals, the complete synthesis is carried out with hydroxy radicals protected in the form of alkoxy radicals, the alkyl radical being eliminated at the end of the reaction in order to recover the free hydroxy radicals.

The processes according to the present invention generally result in a compound corresponding to formula I in the form of a racemic mixture which may be used as it is. However, it may be of interest for certain applications to separate each of the optically inverse forms or enantiomorphs.

For this purpose, it is possible to use the known processes for the separation of enantiomorphs, in particular by the reaction of the racemic mixture with an optically active compound having a determined configuration, to obtain a mixture of two diastereoisomers which may be separated as a result of their different physical properties, for example by fractional crystallisation.

Once the two diastereoisomers have been separated, it is possible to decompose them again in order to restore the two enantiomorphs which are originally present in the racemic mixture.

Of course, the nature of the optically active compounds which are suitable depends on the type of compound corresponding to the formula I which is obtained, or the intermediates and synthesis precursors of I. Thus, for example, if the compound has a carbonyl group (precursor derivative of the alcohol II), it is possible to use an optically active hydrazine, to prepare a diastereoisomeric hydrazone resolvable in particular by fractional crystallisation or by high resolution chromatographic techniques.

Other methods for the resolution of the racemic mixtures may also be used, for example resolution by enzymatic means.

The following schemes illustrate the method of preparation of some starting compounds which may be used in the processes according to the present invention.

SCHEME A

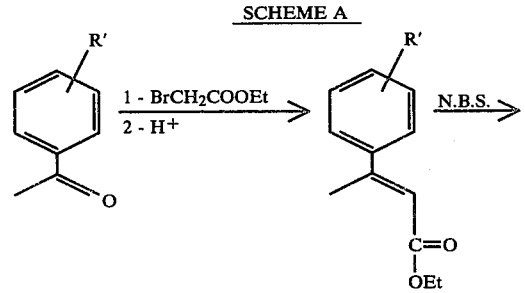

-continued
SCHEME A

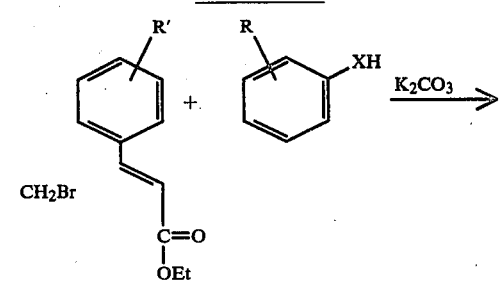

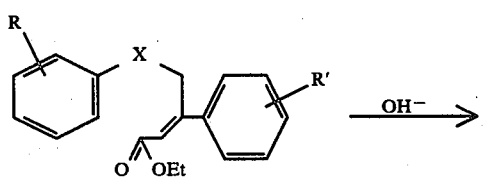

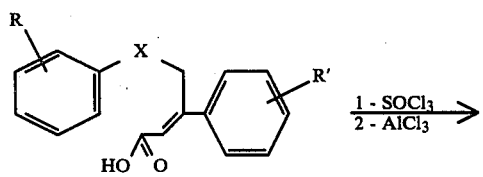

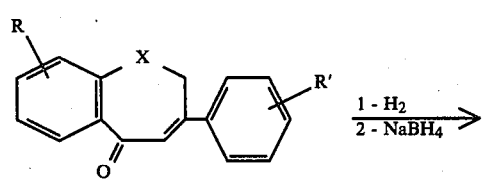

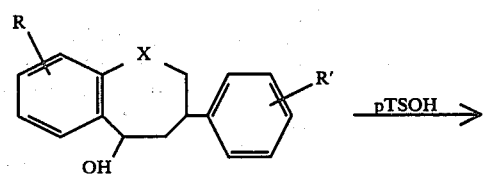

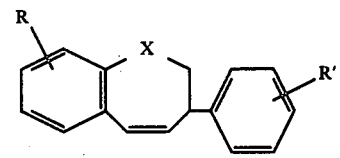

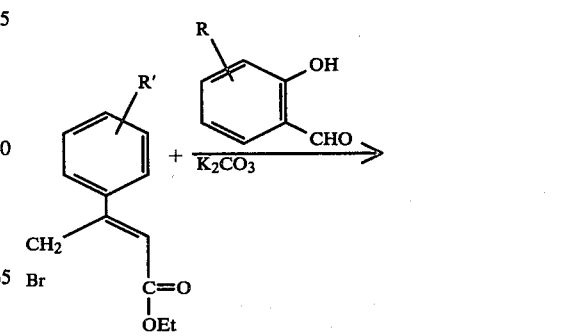

-continued
SCHEME A

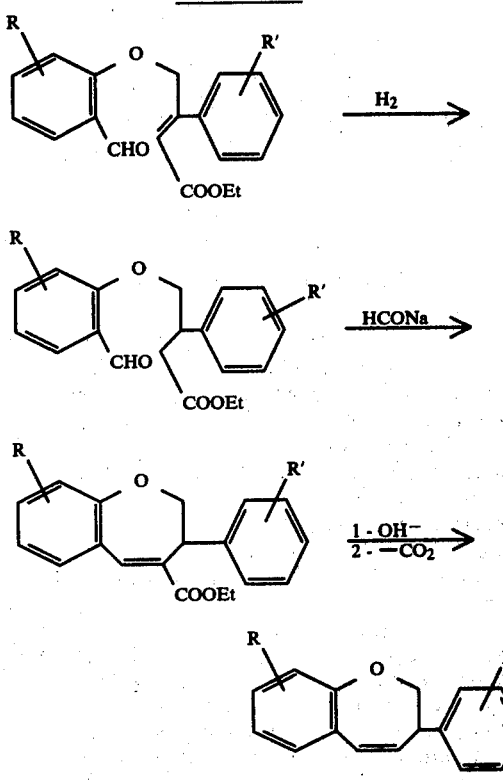

The present invention also relates to the use of the compounds corresponding to formula I as a medicament which is useful in the treatment or disorders in the cardiovascular system and is also useful for the treatment of venous insufficiencies, and of peripheral inflammation and oxygenation.

In the cardiovascular context, the molecules according to the present invention have an anti-hypertensive and/or anti-anginal activity. All these new molecules have a modulated impact on the α-adrenergic receivers and have oxygenator properties on the blood and tissue.

The modulation essentially depends on the nature of the heteroatom X, since it will be demonstrated in the following that the antagonism on the postsynaptic receivers is more considerable when this heteroatom is nitrogen than when it is, in order, oxygen and sulphur. Moreover, the α-lytic character of the molecules is more considerable when the 8-position is substituted by a hydroxy radical, than when this same hydroxy radical is in the 7-position.

The activity of these compounds on venous insufficiencies (post-phlebitic syndrome, ortho static hypotension) is just as valuable as the anti-inflammatory activity, and improving peripheral oxygenation (cerebral, pulmonary or of the limbs).

Taken altogether, the compounds according to this invention are only slightly toxic and their DL 0 is about a few grams per kilogram by oral administration in the case of mice.

These compounds may be used on their own or in admixture with other pharmacologically active compounds in preparations by enteral or parenteral administration.

The following Examples illustrate the preparation of some of the compounds according to the present invention, as well as their pharmacological activity.

EXAMPLE 1

Preparation of 8-methoxy-3-(4-methoxyphenyl)-2,3-dihydro-1-benzoxepine

This derivative is synthesized according to scheme A.

2 500 g of p-methoxy acetophenone which have been treated with ethyl bromoacetate in the presence of zinc according to the method described by J. SCHMITT and Coll. BSCF 1966 p. 953 produce, after dehydration in the presence of p-toluene sulphonic acid and with distillation, ethyl 3-(4-methoxy phenyl)-2-butenoate (1 680 g). BP=135°–155° C./0.1 mm Hg.

This ester is treated under reflux in the presence of carbon tetrachloride with the stoichiometric quantity of N-bromo-succinimide. After concentration and elimination of the succinimide which has formed, ethyl 4-bromo-3-(4-methoxy-phenyl)-2-butanoate (1 500 g) is isolated by crystallisation and is condensed with 3-methoxyphenol in acetone in the presence of potassium carbonate. After being filtered and concentrated, the condensed ester is taken up in butanol and subjected to alkaline hydrolysis by the addition of soda. After being washed and taken up in ethyl acetate, 4-(3-methoxy-phenoxy)-3-(4-methoxyphenyl)-2-butenoic acid, 860 g, is isolated by crystallisation.

This acid is treated with thionyl chloride and then with aluminum chloride in dichloromethane or isolated by filtration on a silica column in order to obtain a mixture of 8-methoxy-2-(4-methoxyphenyl)-2-homochromene-5-one and 8-methoxy-3-(4-methoxyphenyl)-3-homochromene-5-one (220 g). This mixture, in solution in ethyl acetate, is hydrogenated in the presence of palladium/charcoal under a pressure of 10 bars, reduced with sodium borohydride, then dehydrated in the presence of p-toluene sulphonic acid to provide 8-methoxy-3-(4-methoxyphenyl)-2,3-dihydro-1-benzoxepine (200 g) corresponding to the formula:

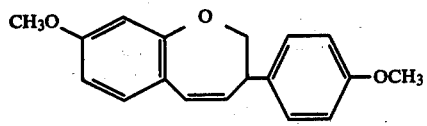

EXAMPLE 2

Preparation of 8-hydroxy-3-(4-hydroxyphenyl)-2,3-dihydro-1-benzoxepine

The product which is obtained in Example 1 is demethylated by heating to 180° in pyridinium chlorohydrate and provides 8-hydroxy-3-(4-hydroxyphenyl)-2,3-dihydro-1-benzoxepine which is purified by filtration over a silica column. The final product which is obtained (110 g) has the following physicochemical characteristics:
Elemental analysis: C 75.25; H 5.57; O 18.95
Molecular weight: 254
Empirical formula: $C_{16}H_{14}O_3$
Solubility: ether, chloroform, ethanol
IR spectrum: Principal bands: 3400, 2900, 1610, 1505 $cm^{-1}$
UV: (MeOH) max. 219 nm, 266 nm, 303 nm.

Mass: M=254 fragments at 147 (C$_9$H$_7$O$_2$) and 107 (C$_7$H$_7$O)
NMR in CD$_3$OD:
7H aromatic between 6.3 and 7.1 ppm 1H (doublet J=12 Hz) at 6.3 ppm
1H (doublet of doublet, J$_1$=12 Hz, J$_2$=5 Hz) at 5.7 ppm
2H (extended singlet) at 4.95 ppm
2H (multiplet) at 4.1 ppm
1H (multiplet) at 3.80 ppm;
NMR diacetylated derivative in CDCl$_3$:
7H aromatic between 6.6 and 7.3 ppm
1H (doublet, J=12 Hz) at 6.4 ppm
1H (doublet of doublet, J$_1$=12 Hz, J$_2$=4 Hz) at 5.9 ppm
2H (multiplet) at 4.2 ppm
1H (multiplet) at 3.9 ppm
6H (singlet) at 2.2 ppm;
NMR $^{13}$C (acetylated derivative) (CDCl$_3$, TMS=0):
20.86 (2 q) 49.4 (d) 74.58 (t) 113.24 (d) 115.77 (d) 121.48 (2 d) 124.19 (s) 127.90 (d) 129.25 (2 d) 132.31 (d) 133.13 (d) 138.14 (s) 150.0 (2 s) 159.56 (s) 169.03 (s) 169.27 (s).

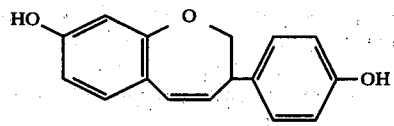

EXAMPLE 3

Preparation of 7-methoxy-3-(4-methoxyphenyl)-2,3-dihydro-1-benzoxepine

This product is synthesized according to scheme B.

Ethyl 4-bromo-3-(4-methoxyphenyl)-2-butenoate, 1 550 g, as obtained in Example 1, is condensed with 2-hydroxy-5-methoxybenzaldehyde, 788 g, in anhydrous acetone in the presence of potassium carbonate. The reaction mixture is, filtered, taken up in isopropyl ether and filtered over silica gel and ethyl 4-(2-formyl-4-methoxyphenoxy)-3-(4-methoxyphenyl)-2-butenoate is crystallised from ethanol (1 710 g).

This condensed derivative is reduced in ethyl acetate in the presence of palladium/charcoal under a pressure of 7 kg of hydrogen, then purified over silica gel to provide 1 395 g of hydrogenated product.

This product is treated with sodium ethylate under reflux and then, after the addition of water, is extracted with chloroform and purified over silica gel to produce 395 g of 7-methoxy-3-(4-methoxyphenyl)-4-(ethoxycarbonyl)-2,3-dihydro-1-benzoxepine. After saponification by soda under reflux with butanol, and after purification over silica gel, 290 of the corresponding acid are isolated.

This acid, heated to 210° C. in the presence of copper chromite and quinoline is decarboxylated to provide, after purification, 7-methoxy-3-(4-methoxyphenyl)-2,3-dihydro-1-benzoxepine (125 g) corresponding to the formula:

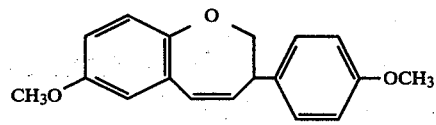

EXAMPLE 4

Preparation of 7-hydroxy-3-(4-hydroxyphenyl)-2,3-dihydro-1-benzoxepine

The above product is demethylated by heating at 180° C. in pyridinium chlorohydrate and produces 7-hydroxy-3-(4-hydroxyphenyl)-2,3-dihydro-1-benzoxepine (165 g). This product has the following physicochemical characteristics:
Elemental analysis: C 75.17 H 5.59 N 18.99
Molecular weight: 254
Empirical formula: C$_{16}$H$_{14}$O$_3$
Solubility: ether, chloroform, ethanol
IR spectrum: Principal bands: 3400, 2900 1610, 1505 cm$^{-1}$
UV: (MeOH) max. 219 nm; 266 nm; 303 nm.
Mass: M=254 fragments at 147 (C$_9$H$_7$O$_2$) and 107 (C$_7$H$_7$O)
NMR in CD$_3$OD:
7 H aromatic between 6.3 and 7.1 ppm
1 H (doublet J=12 Hz) at 6.3 ppm
1 H (doublet of doublet, J$_1$=12 Hz, J$_2$=5 Hz) at 5.7 ppm
2 H (extended singlet) at 4.95 ppm
2 H (multiplet) at 4.1 ppm
1 H (multiplet) at 3.80 ppm;
HPLC: Phase C$_8$—methanol-water $$Tr \frac{\text{8-hydroxy-3-(4-hydroxyphenyl)-2,3-dihydro-1-benzoxepine}}{\text{7-hydroxy-3-(4-hydroxyphenyl)-2,3-dihydro-1-benzoxepine}} = 1$$

EXAMPLE 5

Preparation of 7-diethylaminoethoxy-3-(4-diethylaminoethoxyphenyl)-2,3-dihydro-1-benzoxepine The compound obtained in Example 4 is treated for 4 hours with 1-bromo-2-diethylaminoethane under reflux with acetone in the presence of potassium carbonate. After chromatography over silica gel, 7-diethylaminoethoxy-3-(4-diethylaminoethoxyphenyl)-2,3-dihydro-1-benzoxepine is obtained.

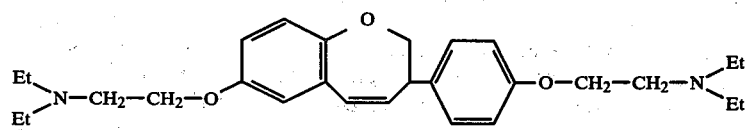

EXAMPLE 6

Preparation of 9-methoxy-3-(4-methoxyphenyl)-2,3-dihydro-1-benzoxepine

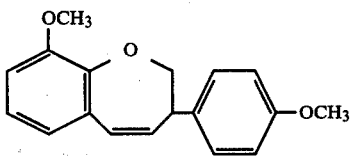

This compound is prepared according to the process described in Example 3 from 4-methoxy acetophenone and 2-hydroxy-3-methoxy-benzaldehyde.

EXAMPLE 7

Preparation of 8-methoxy-3-(3-methoxyphenyl)-2,3-dihydro-1-benzoxepine

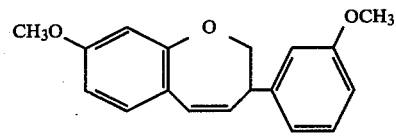

This compound is prepared according to the process described in Example 1 from 3-methoxyacetophenone and 3-methoxyphenol.

EXAMPLE 8

Preparation of 8,9-dimethoxy-3-(4-methoxyphenyl)-2,3-dihydro-1-benzoxepine

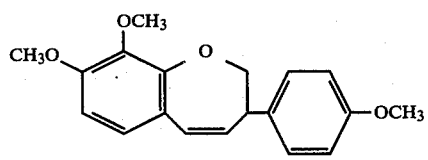

This compound is prepared according to the method described in Example 1 from 4-methoxyacetophenone and 2,3-dimethoxyphenol.

EXAMPLE 9

Preparation of 6,8-dimethoxy-3-(4-methoxyphenyl)-2,3-dihydro-1-benzoxepine

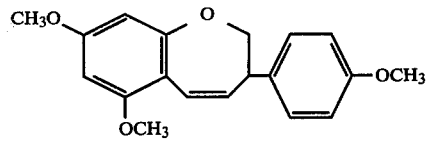

This compound is prepared according to the process described in Example 1 from 4-methoxyacetophenone and 3,5-dimethoxyphenol.

EXAMPLE 10

Preparation of 8-methoxy-3-(3,4-dimethoxyphenyl)-2,3-dihydro-1-benzoxepine

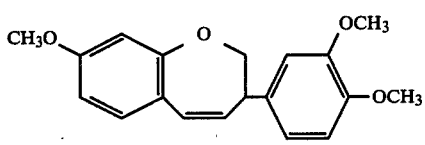

This compound is prepared according to the process described in Example 1 from 3,4-dimethoxyacetophenone and 3-methoxyphenol.

EXAMPLE 11

Preparation of 3-(4-methoxyphenyl)-2,3-dihydro-1-benzoxepine

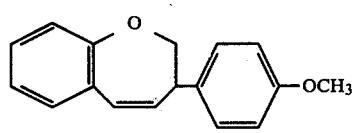

This compound is prepared according to the process described in Example 1 from 4-methoxyacetophenone and phenol.

EXAMPLE 12

Preparation of 8-methoxy-3-(4-methoxyphenyl)-2,3-dihydro-1-benzothiepine

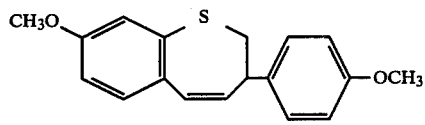

This compound is prepared according to the process described in Example 1 from 4-methoxyacetophenone and 3-methoxybenzenethiol.

EXAMPLE 13

Preparation of 8-chloro-3-(4-methoxyphenyl)-2,3-dihydro-1-benzoxepine

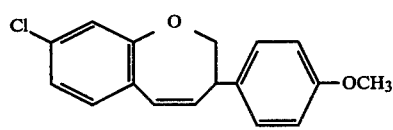

This compound is prepared according to the process described in Example 1 from 4-methoxyacetophenone and 3-chlorophenol.

EXAMPLE 14

Preparation of
8-amino-3-(4-aminophenyl)-2,3-dihydro-1-benzoxepine

This compound is prepared according to the process described in Example 1, with intermediate blocking of the nitrogen function, from 4-aminoacetophenone and 3-aminophenol.

EXAMPLE 15

Preparation of
8-methoxy-3-(4-methoxyphenyl)-2,3-dihydro-1-benzazepine

This compound is prepared according to the process described in Example 1, with intermediate blocking of the nitrogen function, from 4-methoxyacetophenone and 3-aminoanisole.

The compounds according to the present invention have valuable anti-hypertensive and anti-anginal properties.

These properties are demonstrated in the following Examples for two of the compounds of this invention:
the compound of Example 2 (hereafter PM 227)
the compound of Example 4 (hereafter PM 250).

EXAMPLE 16

Cardiovascular activity

The cardiovascular activity was tested in dogs by conventional processes using the right ventricular pressure (RVP), the cardiac frequency (CF), the femoral arterial pressure (FAP), the left ventricular pressure (LVP) and the derivative thereof (dp/dt).

The following Table 1 shows the average results in percentage variation with respect to the control period (base 100).

TABLE 1

|  | Dogs not treated with atropine | | | | | Dogs treated with atropine | | | | |
| --- | --- | --- | --- | --- | --- | --- | --- | --- | --- | --- |
|  | RVP | CF | FAP | LVP | dP/dt | RVP | CF | FAP | LVP | dP/dt |
| PM 250 0.1 mg/kg | 120 | 110 | 80 | 85 | 85 | 140 | 95 | 105 | 100 | 100 |
| PM 227 0.1 mg/kg | 110 | 95 | 104 | 105 | 103 | 120 | 90 | 90 | 105 | 102 |

If the preliminary injection of 0.5 µg/kg of noradrenaline is taken as the 100 basis, the modulation over this position clearly appears in Table 2.

TABLE 2

|  | Dogs not treated with atropine | | | | | Dogs treated with atropine | | | | |
| --- | --- | --- | --- | --- | --- | --- | --- | --- | --- | --- |
|  | RVP | CF | FAP | LVP | dP/dt | RVP | CF | FAP | LVP | dP/dt |
| PM 250 0.1 mg/kg | 95 | 115 | 110 | 100 | 100 | 100 | 95 | 85 | 95 | 95 |
| PM 227 0.1 mg/kg | 90 | 110 | 130 | 105 | 104 | 115 | 85 | 55 | 88 | 90 |

A muscarinic component is observed over the α presynaptic receivers which appears for PM 227 and is very discrete for the other.

EXAMPLE 17

Oxygenator properties of the blood

These two compounds have the same oxygenator blood properties, the only difference appearing in the length of activity. PM 227 has an activity which continues for more than two hours after injection, whereas the activity of PM 250 terminates between 1 and 1½ hours.

The following Table 3 shows the consumption of cardiac oxygen (mVO$_2$) and the pulmonary arteriovenous difference ($\Delta$PO$_{2p}$) for the two products on a basis of 100 with respect to the reference period.

TABLE 3

| Parameters | | | | | | | | | | | | | | |
| --- | --- | --- | --- | --- | --- | --- | --- | --- | --- | --- | --- | --- | --- | --- |
|  | PM 250 (0.1 mg/kg) | | | | | | | PM 227 (0.1 mg/kg) | | | | | | |
|  | Time (minutes) | | | | | | | | | | | | | |
|  | 5 | 10 | 20 | 30 | 60 | 90 | 120 | 5 | 10 | 20 | 30 | 60 | 90 | 120 |
| mVO$_2$ | 90 | 85 | 85 | 90 | 95 | 100 | 100 | 80 | 75 | 75 | 90 | 85 | 78 | 80 |
| $\Delta$PO$_{2p}$ | 100 | 105 | 110 | 110 | 105 | 102 | 100 | 102 | 110 | 130 | 130 | 125 | 130 | 120 |

This Example clearly shows the modulations provided by the different substituents and their relative importance.

Likewise, it is possible to see a modulation on the anti-agregant activity with respect to collagen, but without the structure-activity relations being as clear. This relatively weak activity (between 10$^{-5}$ and 10$^{-4}$ M) is in fact only a supplementary asset in the activities claimed above in the cardiovascular aspect, that is:

hypertensive disorders and cardiopathic disorders, more particularly that of anginal origin.

We claim:

1. A compound corresponding to formula I:

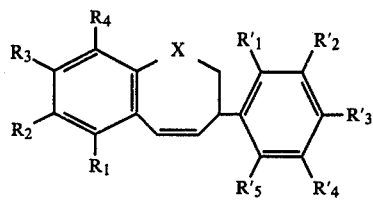

wherein

X represents oxygen;

$R_1$ to $R_4$, and $R'_1$ to $R'_5$ independently represent the following:

a hydrogen atom, a $C_1$ to $C_5$ alkoxy or a $C_2$ to $C_5$ acyloxy radical, a hydroxy radical, a hydroxy $C_1$ to $C_5$ alkoxy, mono- or di- $C_1$ to $C_5$ alkyl amino $C_1$ to $C_5$ alkoxy radical.

2. A compound according to claim 1, characterised in that the radicals $R_1$ to $R_4$ and $R'_1$ to $R'_5$ independently represent a hydrogen atom, or a hydroxy or methoxy radical.

3. A compound according to claim 2, characterised in that it has the formula:

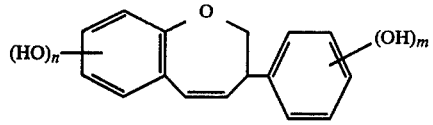

wherein n is an integer from 0 to 2, and m is an integer from 0 to 3.

4. A compound according to claim 3 corresponding to the formula:

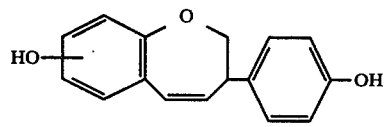

5. A pharmaceutical composition comprising a compound according to one of claims 1 to 4 and a pharmaceutically acceptable carrier.

* * * * *